United States Patent [19]
Kopp et al.

[11] 4,431,019
[45] Feb. 14, 1984

[54] FLUID FLOW CONTROL DEVICE

[75] Inventors: Clinton V. Kopp; James Hitchcock, both of Barrington; Martin Miller, Lake-in-the-Hills, all of Ill.

[73] Assignee: Baxter Travenol Laboratories, Inc., Deerfield, Ill.

[21] Appl. No.: 277,414

[22] Filed: Jun. 25, 1981

[51] Int. Cl.³ .................. B01D 31/00; F16K 31/365
[52] U.S. Cl. .................................. 137/87; 251/61.1; 210/433.2; 210/637
[58] Field of Search ................... 137/87, 98, 100; 251/61.1; 128/214 B, 214 R, 274; 210/137, 433.2, 637

[56] References Cited

U.S. PATENT DOCUMENTS

| | | |
|---|---|---|
| 1,524,217 | 1/1925 | Small . |
| 2,296,833 | 9/1942 | Boynton . |
| 2,416,161 | 2/1947 | Deck . |
| 2,572,175 | 10/1951 | McPherson .................. 251/61.1 |
| 2,736,332 | 2/1956 | Simmons . |
| 2,837,102 | 6/1958 | Bauer et al. .................. 137/98 |
| 2,850,038 | 9/1958 | Shabaker . |
| 2,857,803 | 10/1958 | Reinecke et al. . |
| 2,905,431 | 9/1959 | Gilbert .................. 251/61.1 |
| 2,943,643 | 7/1960 | Pinter et al. . |
| 2,992,652 | 7/1961 | Fellberg .................. 251/331 |
| 3,083,943 | 4/1963 | Stewart, Jr. et al. .................. 251/61.1 |
| 3,170,477 | 2/1965 | Scott, Jr. et al. .................. 137/183 |
| 3,319,926 | 5/1967 | Boger . |
| 3,465,752 | 9/1969 | Brychta et al. . |
| 3,490,479 | 1/1970 | Mott et al. .................. 251/61.1 |
| 3,693,611 | 9/1972 | Ploss . |
| 3,779,267 | 12/1973 | Cowan . |
| 3,807,426 | 4/1974 | Henes .................. 128/274 |
| 3,853,147 | 12/1974 | Cibulka . |
| 3,856,046 | 12/1974 | Brown et al. .................. 251/61.1 |
| 3,917,162 | 11/1975 | Trotter et al. .................. 137/87 |
| 3,957,073 | 5/1976 | Barnum .................. 137/87 |
| 4,089,342 | 5/1978 | Stradella et al. .................. 137/599 |
| 4,142,523 | 3/1979 | Stegeman . |
| 4,178,938 | 12/1979 | Au . |
| 4,181,245 | 1/1980 | Garrett et al. . |
| 4,274,452 | 6/1981 | Schmitt .................. 251/61.1 |
| 4,304,260 | 12/1981 | Turner et al. .................. 251/61.1 |
| 4,321,939 | 3/1982 | Fenwick .................. 137/87 |

Primary Examiner—Alan Cohan
Assistant Examiner—John A. Rivell
Attorney, Agent, or Firm—Paul C. Flattery; Daniel D. Ryan

[57] ABSTRACT

A fluid flow control device comprises first, second, and third fluid conduits. The first and second conduits are adapted to communicate with separate sources of pressurized fluid. The third conduit includes an inlet portion in direct flow communication with the first conduit and an outlet portion communicating with the atmosphere. A flexible wall forms an interface between portions of the second and third conduits. In response to fluid pressure fluctuations in the second conduit, the flexible wall simultaneously meters the flow communication through both the inlet and outlet portions of the third conduit. The fluid pressure in the first conduit is thereby elevated until substantial equilibrium with the fluid pressure in the second conduit occurs.

5 Claims, 5 Drawing Figures

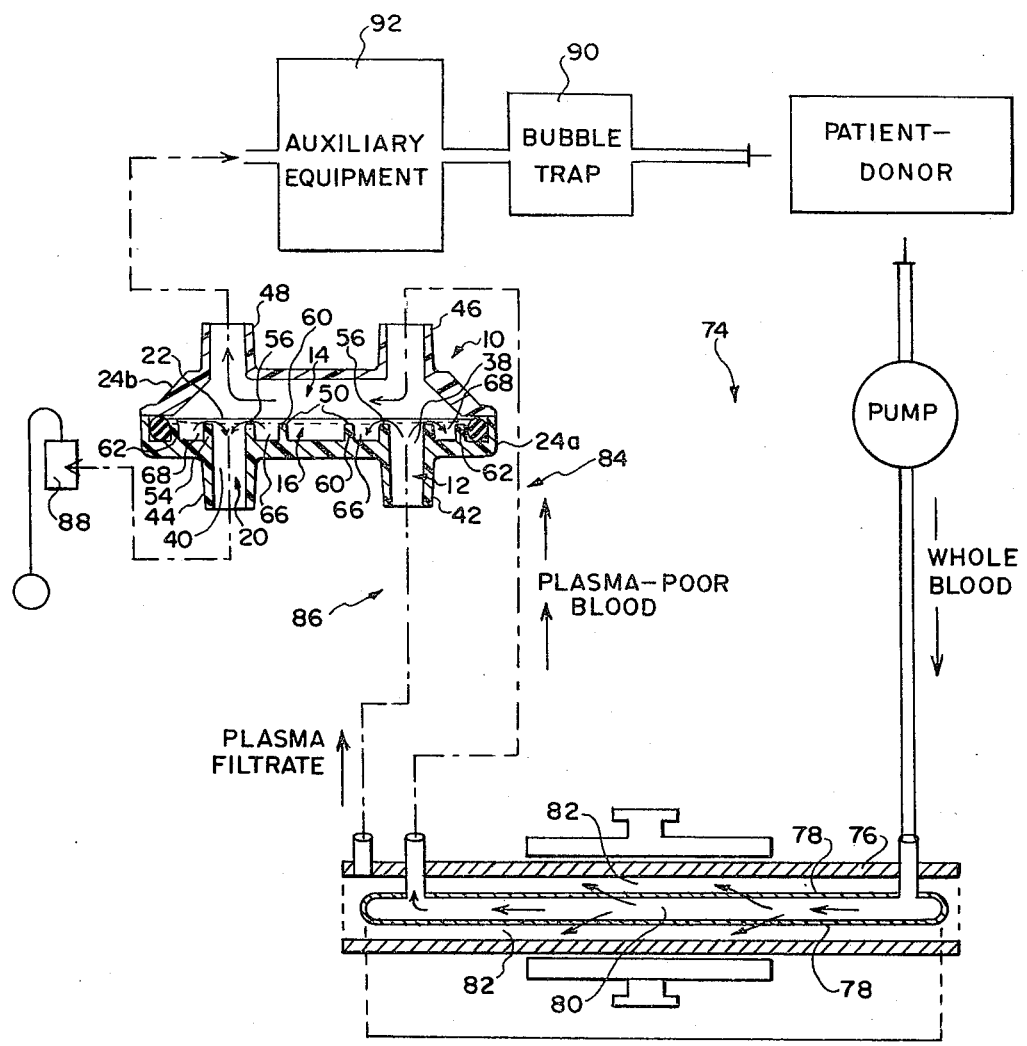

FLUID FLOW CONTROL DEVICE

FIELD OF THE INVENTION

This invention generally relates to fluid flow control devices, and, more particularly, to fluid flow control devices which serve to control fluid pressures.

DESCRIPTION OF THE PRIOR ART

Attention is directed to the following United States Patents which concern various fluid pressure regulating and flow control devices:

| Small | 1,524,217 | January 27, 1925 |
| --- | --- | --- |
| Boynton | 2,296,833 | February 18, 1947 |
| Deck | 2,416,161 | February 18, 1947 |
| Shabaker | 2,850,038 | September 2, 1958 |
| Reinecke et al | 2,857,803 | October 28, 1958 |
| Pinter et al | 2,943,643 | July 5, 1960 |
| Boger | 3,319,926 | May 16, 1967 |
| Brychta et al | 3,465,752 | September 9, 1969 |
| Ploss | 3,693,611 | September 26, 1972 |
| Cowan | 3,779,267 | December 18, 1973 |
| Cibulka | 3,853,147 | December 10, 1974 |
| Au | 4,178,938 | December 18, 1979 |
| Stegeman | 4,142,523 | March 6, 1979 |
| Garrett et al | 4,181,245 | January 1, 1980 |

Attention is also directed to two pending U.S. patent applications entitled "MEMBRANE PLASMAPHERESIS APPARATUS AND METHOD" (Clint Kopp and James Hitchcock) and "FLUID FLOW CONTROL DEVICE" (Clint Kopp and James Hitchcock), both of which share the same filing date as this application and which are assigned to the assignee of this invention.

One of the principal objects of this invention is to provide a fluid flow control device which is adapted for use in any system in which the control of fluid pressure is desirable, which operates with a minimum of moving parts, and which lends itself to relatively efficient and inexpensive manufacturing techniques.

Another principal object of this invention is to provide a fluid flow control device which includes redundancy in its design to assure consistent and uninterrupted operation.

Yet another principal object of this invention is to provide a fluid flow control device which is suitable for metering the flow of human blood or other parenteral solutions and which can constitute an essentially disposable unit.

SUMMARY OF THE INVENTION

To achieve these and other objects, the invention provides a fluid flow control device comprising first, second, and third conduit means. The first and second conduit means are each adapted to communicate with a separate source of pressurized fluid and serve to conduct pressurized fluid from the associated source. The third conduit means conducts pressurized fluid from the first conduit means and includes an inlet portion, which conducts pressurized fluid from the first conduit means into the third conduit means, and an outlet portion, which conducts pressurized fluid out of the third conduit means. The third conduit means further includes generally flexible wall means which forms an interface with a portion of the second conduit means. The flexible wall means is operative in response to fluid pressures in the second conduit means for metering the conduction of pressurized fluid through both the inlet and outlet portions of the third conduit means. The metering action of the flexible wall means adjusts the fluid pressure in the first conduit means, until it achieves substantial equilibrium with the fluid pressure then existent in the second conduit means. Furthermore, should the flexible wall means fail to properly meter the conduction through one of the inlet and outlet portions, the ongoing, simultaneously metering of the other inlet and outlet portion assures a steady, uninterrupted operation.

In one embodiment, the fluid flow control device includes means for defining more than a single path for the fluid traversing the third conduit means to follow. Thus, should one flow path become blocked or obstructed, there is another flow path to assure uninterrupted fluid conduction.

In one embodiment, the device takes the form of a compact housing which lends itself to the efficient manufacture from plastic materials suited for contact with parenteral fluids and the like.

Other features and advantages of the invention will be pointed out in, or will be apparent from, the specifications and claims, as will obvious modifications of the embodiments shown in the drawings.

DESCRIPTION OF THE DRAWINGS

FIG. 5 is a diagrammatic view of the fluid flow control device shown in FIGS. 1 through 4 used in association with a membrane plasmapheresis apparatus.

Figure 1:
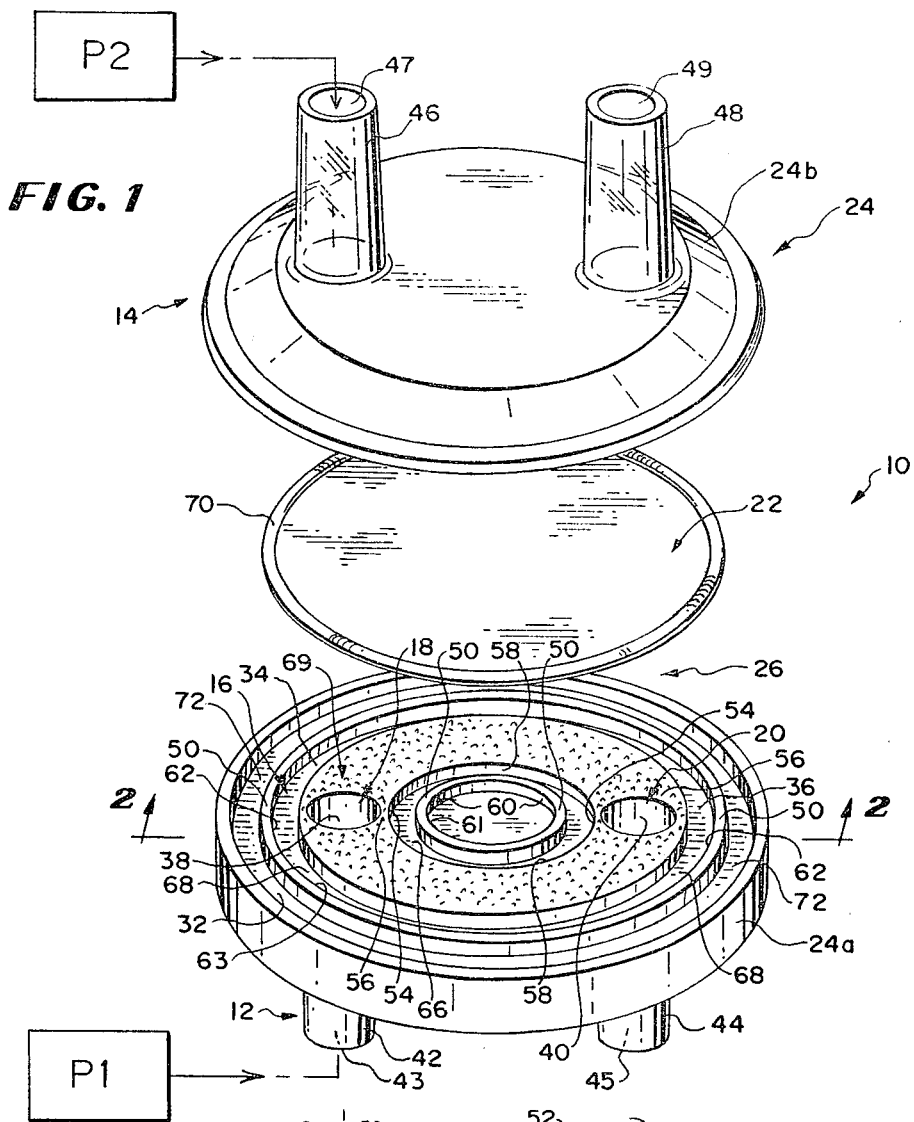
FIG. 1 is an exploded perspective view of a fluid control device which embodies various of the features of the invention.

Before explaining the embodiments of the invention in detail, it is to be understood that the invention is not limited in its application to the details of construction and the arrangement of components set forth in the following description and as illustrated in the drawings. The invention is capable of other embodiments and of being practiced and carried out in various ways. Also, it is to be understood that the phraseology and terminology used herein is for the purpose of description and should not be regarded as limiting.

DESCRIPTION OF THE PREFERRED EMBODIMENT

Figure 2:
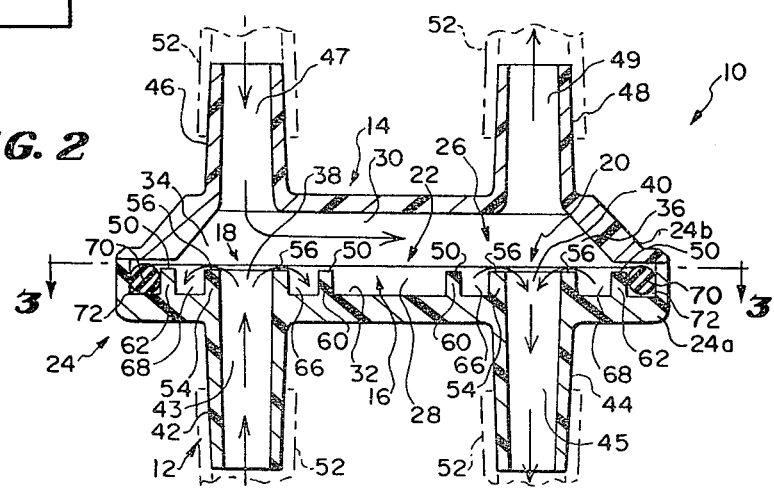
FIG. 2 is an assembled section view of the fluid flow control device taken generally along line 2—2 in FIG. 1.

A fluid flow control device 10 is shown in FIGS. 1 and 2. The device 10 includes first, second, and third conduit means, respectively, 12, 14, and 16. The first and second conduit means 12 and 14 are each adapted to communicate with a separate source of pressurized fluid (generally designated P1 and P2 in FIG. 1), and each serves to conduct pressurized fluid from the associated source.

The third conduit means 16 serves to conduct pressurized fluid from the first conduit means 12 and, for this purpose, includes an inlet portion 18, which is in direct flow communication with the first conduit means 12, as well as an outlet portion 20, which is spaced from the inlet portion 18 and is in flow communication with the atmosphere.

The third conduit means 16 also includes flexible wall means 22 which forms an interface with a portion of the second conduit means 14 (see FIG. 2). The flexible wall means 22 is operative, in response to fluid pressures in the second conduit means 14, to simultaneouly meter the conduction of pressurized fluid through both the inlet and outlet portions 18 and 20 of the third conduit means 16. Substantial equilibrium between the fluid pressures in the first and second conduit means 12 and 14 is thereby established and maintained by the device 10.

The device 10 as heretofore described may be variously constructed, depending upon the particular operative objectives and environment in which use is contemplated. In the illustrated embodiment (as best seen in FIGS. 1 and 2), the device 10 includes a compact housing 24 in which an open interior area 26 is defined. The flexible wall means 22 extends transversely across this interior area 26 and thereby compartmentalizes the area 26 into two chambers 28 and 30. One of the chambers, which will hereafter be referred to as the first chamber 28, forms a portion of the heretofore described third conduit means 16. The other chamber, which will hereafter be referred to as the second chamber 30, forms a portion of the heretofore described second conduit means 14.

The housing 24 itself may be variously constructed. However, in the illustrated embodiment (and see, in particular, FIG. 1), the housing 24 includes first and second generally circular housing portions, which are designated 24a and 24b, between which the flexible wall means 22 is sandwiched. The first chamber 28 is formed within the housing portion 24a, and the second chamber 30 is formed within the housing portion 24b.

As can best be seen in FIG. 2, the first chamber 28 is peripherally bounded on one side by the flexible wall means 22 and on another side by an interior wall or surface 32 of the housing portion 24a. The interior wall 32 directly faces the flexible wall means 22. Furthermore, the first chamber 28 includes laterally spaced ends 34 and 36, and the inlet and outlet portions 18 and 20 of the third conduit means 16 include, respectively, an inlet opening 38 formed in the interior wall 32 in the chamber end 34 and a corresponding outlet opening 40 formed in the interior wall 32 in the other chamber end 36.

In this arrangement (see FIGS. 1 and 2), the first conduit means 12 takes the form of a first, generally rigid member 42 which extends outwardly from the housing portion 24a. The member 42 includes a bore 43 which constitutes a fluid passage leading to the inlet opening 38 of the first chamber 28.

The outlet portion 20 of the third conduit means 16 similarly includes a second generally rigid member 44 which extends outwardly from the same housing portion 24a. The member 44 also includes a bore 45 which constitutes a fluid passage leading from the outlet opening 40 of the first chamber 28.

In the illustrated construction, the inlet and outlet openings 38 and 40 are generally diametrically spaced across from each other in the first chamber 28 (see FIGS. 1 and 3), and the first and second members 42 and 44 are correspondingly spaced on the exterior of housing portion 24a.

Similarly, the second conduit means 14 includes laterally spaced third and fourth generally rigid members, respectively 46 and 48, which extend outwardly from the other housing portion 24b. The members 46 and 48 each include a bore, respectively 47 and 49, which constitute inlet and outlet fluid passages leading into and out of the second chamber 30.

Each of the outwardly extending rigid members 42, 44, 46 and 48 are suited to accommodate lengths of flexible tubing 52 (shown in phantom lines in FIG. 2), which serve to conduct pressurized fluids to and from the device 10. As shown in FIGS. 1 and 2, the members 42, 44, 46, and 48 are preferably tapered at their outer end portions to facilitate their attachment to the flexible tubing 52.

Figure 4:
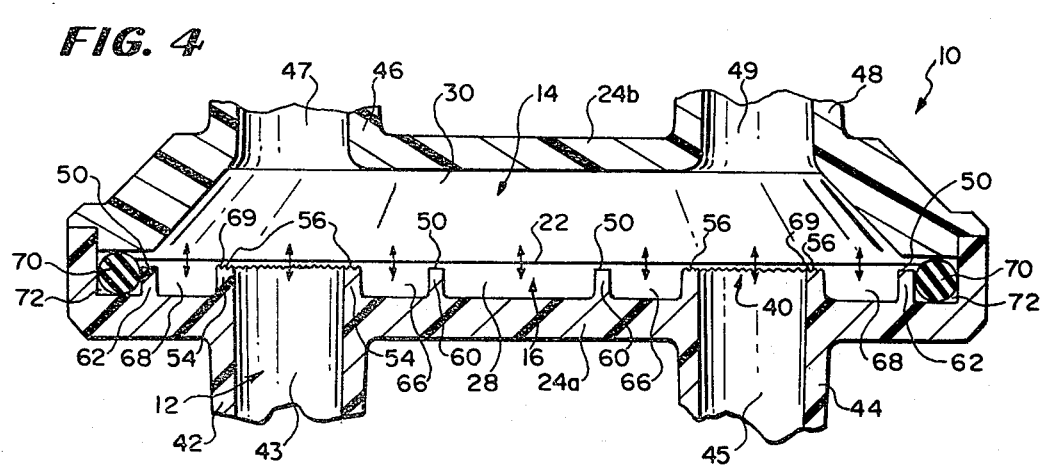
FIG. 4 is an enlarged section view of the interior portion of the device.

As best seen in FIGS. 1, 2 and 4, the inlet and outlet openings 38 and 40 of the first chamber 28 are each circumferentially enclosed by an upstanding annular member 54 which extends axially of the respective openings 38 and 40 outwardly from the interior wall 32 and into the first chamber 28. Each member 54 terminates in a generally planar surface 56 (as best seen in FIG. 4) which extends in a close, normally non-contiguous relationship with the flexible wall means 22 when there are no fluids being conducted through the first and second chambers 28 and 30.

Figure 3:
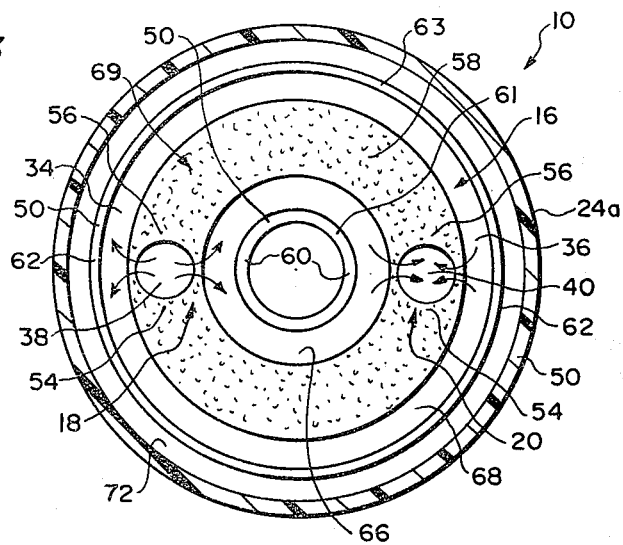
FIG. 3 is a top view of the device generally taken along line 3—3 in FIG. 2.

While the members 54 associated with the openings 38 and 40 can each constitute a separate annular structure, in the generally circular configuration of the housing 24 in the illustrated embodiment, the members 54 are part of a continuous upstanding circular ridge 58 formed within the first chamber 28 (see FIGS. 1 and 3).

Second and third members 60 and 62 are diametrically spaced, respectively, inwardly and outwardly of each of the first mentioned annular members 54 (see FIGS. 2 and 4). Like the annular members 54, the second and third members 60 and 62 each terminates in a generally planar surface 50 which faces the flexible wall means 22 in the same close, normally non-contiguous relationship as the members 54; this is, the distance between the surfaces 50 and the flexible wall means 22 is generally the same as the comparable distance between the surfaces 56 and the flexible wall means 22.

The members 60 and 62 serve as points of support for the flexible wall means 22 radially inwardly and outwardly of the planar surfaces 56 and assure that the wall means 22 is maintained in a generally planar configuration with respect to the surfaces 56, notwithstanding movement, or flexing, of the flexible wall means 22 toward the interior surface 32. This enhances the overall metering effect of the flexible wall means 22.

The members 60 and 62 can constitute various shapes to serve this support junction. However, corresponding to the "single-ridge" construction of the members 54 of the illustrated embodiment, (i.e., the single ridge 58), the second and third shoulders 60 and 62 are each a part of corresponding second and third upstanding circular ridge 61 and 63, which ridges 61 and 63 are respectively positioned concentrically inwardly and outwardly of the first mentioned ridge 58.

Together, the ridges 58, 61 and 63 provide points of support along the entire span of the flexible wall means 22. The ridges 58, 61, and 63 thus prevent the flexible wall means 22 from assuming an outwardly bowed or convex configuration in the first chamber 28, particularly in the interval between the inlet and outlet openings 38 and 40. This promotes a smooth and even metering of the fluid flow into and out of the first chamber 28.

The third conduit means 16 further includes means defining more than one fluid path or channel for conducting fluid through the first chamber 28. The particular number and configuration of the flow paths utilized can vary according to the specific interior configuration of the first chamber 28. In the generally circular configuration of the illustrated embodiment (as best seen in FIG. 3), a first, or inner, fluid flow path 66 is formed between the adjacent concentric ridges 58 and 61, and a second, or outer, fluid flow path 68 or channel is formed between the adjacent concentric ridges 58 and 63.

Referring now principally to FIG. 4, when a condition exists in which the fluid pressure in the second chamber 30 exceeds the fluid pressure in the first conduit means 12 (and, hence, in the first chamber 28 as well), the flexible wall means 22 will be displaced by the pressure differential away from the second chamber 30 and, thus, toward the surfaces 56 which circumferentially enclose the inlet and outlet openings 38 and 40 of the first chamber 28. This movement is generally shown by arrows in FIG. 4.

Because of the close proximity of the flexible wall means 22 to the planar surfaces 56, the flow of pressurized fluid through both the inlet and outlet openings 38 and 40 will be metered, or restricted, simultaneously, though independently, and by generally the same amount. This restriction generates resistance, or back pressure, to the flow of pressurized fluid in the first conduit means 12. This back pressure, in turn, causes the fluid pressure in the first conduit means 12 to rise. The elevation in fluid pressure in the first conduit means 12 will continue until a "steady state" condition is achieved in which the pressure in the first conduit means 12 equals the pressure in the second conduit means 14.

It should be appreciated that the particular position of the flexible wall means 22 relative to each of the surfaces 56 necessary to bring about this state of pressure equalization will depend upon the particular magnitudes of the then prevailing pressures in the first and second chambers 28 and 30, as well as the then prevailing fluid flow rates through the first and second chambers 28 and 30.

Should the fluid pressure in the second chamber 30 subsequently increase or decrease, the flexible wall means 22 will correspondingly change its position relative to each of the surfaces 56 by moving toward a new position, respectively, closer to or farther away from the surfaces 56. This automatically changes the previously imposed restriction to the fluid flow through each of the openings 38 and 40 in lieu of a new restriction. The conduction of fluid into and out of the first chamber 28 will thus be metered at a new rate until a new state of equilibrium at the higher or lower fluid pressure level occurs.

The flexible wall means 22 is thus movable through a range of positions which are progressively spaced closer to or farther away from the surfaces 56. The particular position assumed by the flexible wall means within this range will depend upon the particular fluid pressures and flow rates then prevailing.

It should be appreciated that the movement of the flexible wall means 22 as just described occurs virtually instantaneously with pressure fluctuations occurring within the second chamber 30. Thus, the device 10 is operative to continuously and automatically maintain pressure equilibrium between the first and second conduit means 12 and 14.

In the illustrated and preferred embodiment, the planar surfaces 56 facing the flexible wall means 22 include a grooved or roughened outer configuration 69. This roughened configuration 69 serves to break any surface tension that might develop between the planar surfaces 56 and the closely adjacent flexible wall means 22. The configuration 69 thus prevents the flexible wall means 22 from completely seating against the planar surfaces 56 to completely block fluid flow through the associated opening 38 and 40. A continuous conduction of pressurized fluid into and through the first chamber 28 is thus maintained by the device 10, notwithstanding the continuous and automatic metering of the flexible wall means 22 and its continuously close proximity to the surfaces 56. Furthermore, periodic spikes of pressure in the first conduit means 12, occassioned by intermittent closure of either the inlet or outlet openings 38 and 40, are virtually eliminated.

In the illustrated embodiment, the entire extent of the ridge 58 facing the flexible wall means 22 is roughened to any break surface tension with the wall means 22 along this area.

The provision of two independent flow paths 66 and 68 within the first chamber 28 and the simultaneous, though independent, metering of each of the inlet and outlet openings 38 and 40 by the flexible wall means 22, provide redundancy in the design of the device 10. Thus, for whatever reason, should the flexible first wall means 22 fail to properly meter the conduction of fluid flow through either one of the openings 38 or 40, the ongoing independent metering of the other opening 38 or 40 will continue to maintain and establish the condition of substantial equilibrium desired. Furthermore, for whatever reason, should one of the flow paths 66 or 68 in the first chamber 28 become blocked or obstructed, the other open flow path 66 or 68 will continue to conduct the fluid through the first chamber 28.

While the device 12 may be variously manufactured, in the illustrated embodiment, the first and second housing portions 24a and 24b constitute separately molded plastic pieces, such as from an injection molded, polyvinyl chloride plastic or plexiglass material. The three ridges 58, 61, and 63 and the fluid flow paths 66 and 68 positioned therebetween form integrally molded portions of the housing portions 24a, as are the outwardly extending members 42 and 44. The same is true for the second chamber 30 and members 46 and 48 associated with the housing portion 24b.

In this construction, the flexible first wall means 22 takes the form of a generally circular diaphragm made of silicon rubber or the like. The diaphragm 22 includes an annular ring 70, and the housing portion 24a includes a corresponding annular groove 72 in which the ring 70 is seated when the housing portions 24a and 24b are properly assembled together, such as by heat or solvent bonding, or by encapsulation. This assembly assures that the flexible diaphragm 22 remains generally uniformly planar within the housing 24 and does not become wrinkled, warped or otherwise incorrectly positioned during the manufacturing or use. This assembly also serves to seal the first and second chambers 28 and 30 from each other to prevent the intermixing of fluids between the first and second conduit means 12 and 14.

This compact structural arrangement also lends itself to construction utilizing a relatively few pre-formed pieces and a minimum of moving parts. The device 10 can thus be manufactured in an efficient and economical manner and constitute an essentially disposable unit. It also lends itself well to construction utilizing only plastic materials and the like which have been approved for contact with human blood or other parenteral fluids.

The device 10 as heretofore described is applicable for use in numerous diverse environments. As is shown in FIG. 5, the device 10 is particularly well suited for use to stabilize the transmembrane pressure of a membrane plasmapheresis apparatus 74.

In this environment, the apparatus 74 includes a module 76 or cell defining a housing in which two sheets 78 of a microporous membrane having a pore size of about 0.1 micron to 2 microns are positioned in a facing, spaced-apart relationship. A fluid path 80 is thus formed between the interior surfaces of the membranes. Open volumes 82 are also formed between the outer surfaces of the membranes and the interior surfaces of the housing. Alternately, a module (not shown) in which a cluster of hollow fiber membranes is supported can be utilized in lieu of the sheet membranes shown in FIG. 5.

In normal operation, whole blood, typically from a patient-donor, is pumped under a predetermined pressure through the fluid path 80 between the sheet membranes 78. The whole blood experiences a determinable pressure drop as it proceeds across the length of the module 76. This causes the red cells, leukocytes, and platelets (known collectively as plasma-poor blood) to proceed in a laminar path across the inner surfaces of the membranes 78, typically for return to the donor via a transfusion set 84. A transmembrane pressure is also generated which, when within a desirable range of between 50 mmHg and 100 mmHg, acts as a driving force to cause the plasma to pass through the pores of the membranes 78 into the volumes 82. A collection conduit 86 communicates with the volumes 82 for transmitting the plasma filtrate to an external container or bag 88. However, should the transmembrane pressure exceed a critical level (approximately 120 mmHg), red cells can themselves be driven into the pores of the membranes 78 and be damaged or destroyed, causing hemolysis.

To stabilize the transmembrane pressure within acceptable levels, the fluid control device 10 as illustrated in FIGS. 1 through 4 is connected downstream of the module 76 in flow communication with both the transfusion set 84 and the plasma collection conduit 86. More particularly, the first member 42 (i.e., the first conduit means 12 of the device 10), is attached in flow communication with the plasma filtrate volumes 82 downstream of the module 76, and the second member 44 (i.e., part of the outlet portion 20 of the third conduit means 16) is attached in flow communication with the plasma collection container 88.

As a result of this interconnection, plasma filtrate flows out of the volumes 82, subject to a determinable plasma pressure, through the first conduit means 12, and thence into and through the third conduit means 16 on its route to the plasma collection container 88, subject to metering by the flexible wall means 22.

The inlet and outlet members 46 and 48 of the second conduit means 14 are connected in-line with the transfusion set 84 downstream of the module 76 and upstream of a bubble trap 90 and any auxiliary equipment 92 (such as a blood warmer) associated with the apparatus 74.

As a result of this in-line connection, the plasma-poor blood exiting the fluid path 80 flows through the second conduit means 14, subject to any back pressure or fluid flow resistance generated by equipment downstream of the module 76. The blood pressure of the patient-donor and any movement of his or her arm during the procedure can also contribute to the back pressure.

At the outset of the plasmapheresis procedure, a pressure differential will virtually always exist between the plasma pressure, which is typically at 0 mmHg, and the backside blood pressure, which typically fluctuates randomly between 20 mmHg and 150 mmHg.

By virtue of the pressure differential between the first chamber 28 (at the plasma pressure) and the second chamber 30 (at the then prevailing backside blood pressure), the flexible first wall means 22 of the device 10 will be immediately displaced as heretofore described toward the surfaces 56 associated with the inlet and outlet openings 38 and 40. This is generally shown by arrows and phantom lines in FIG. 5. This serves to restrict the flow of plasma filtrate into and through the first chamber 28. The plasma pressure entering the first chamber 28 will thus be elevated, until it reaches a state of substantial equilibrium with the backside blood pressure.

It has been observed that, when this state of equilibrium between the plasma pressure and backside blood pressure exists, the magnitude of the transmembrane pressure is stabilized and not effected by ongoing fluctuations in the backside pressure.

The device 10 will thereafter operate to maintain this equilibrium, notwithstanding subsequent variations in the backside blood pressure. Furthermore, as heretofore described, the device 10 will also operate to maintain a continuous flow of plasma filtrate and plasma-poor blood downstream of the module 76.

The fluid flow control device 10 of the present invention can be of various sizes, according to the operational environment in which it is used. In one embodiment suited for operation under the pressures conditions normally encountered during membrane plasmapheresis operations, the housing 24 is approximately 2.0 inches in overall diameter. The maximum depth of the first chamber 28 is approximately 0.09 inch, and the corresponding maximum depth of the second chamber is approximately 0.17 inch. In this embodiment, the height of the ridges 58, 61, and 63 extending within the first chamber 28 is approximately 0.04 inch, and the width of the circular flow paths 64 and 66 is approximately 0.15 inch.

In this operative environment, the diaphragm (i.e., the flexible wall means 22) has a thickness of about 0.0015 inch, and the normal interval between the diaphragm 22 and the surfaces 50 and 56, absent fluid flow in the first and second chambers, is approximately 0.005 inch. Also in this operative embodiment, the roughened configuration 68 of the surfaces 56 constitutes a number 32 EDM finish.

Use of this operative embodiment of the device 10 in association with the apparatus 74 has been observed to stabilize the transmembrane pressure, regardless of the magnitude of the then existent backside pressure, at a magnitude which represents only the flow resistance of the module 76 itself, which is a quantity under direct operator control. In particular, when an inlet blood pressure of between 150 mmHg and 200 mmHg and a pressure drop across the module 76 of approximately 100 mmHg are maintained by the operator, the device 10 serves to stabilize the transmembrane pressure within the operationally desirable range of between 50 mmHg and 100 mmHg, even though the backside pressure may at the same time be undergoing random fluctuations of between 20 mmHg and 150 mmHg.

In addition, the device 12 has been observed to continuously maintain an uninterrupted flow of plasma filtrate from the module 76 and through the first and third conduit means 12 and 16 at a rate of between 10 cubic centimeters per minute and 80 cubic centimeters per minute. At the same time, the device 10 has been observed to continuously maintain an uninterrupted flow of plasma-poor blood from the module 76 and through the second conduit means 14 at a rate of between 40 cubic centimeters per minute and 300 cubic centimeters per minute.

Use of the fluid flow control device 10 in association with the apparatus 76 permits the use of operationally desirable components of membrane plasmapheresis, such as a smaller, more comfortable needle, and auxiliary equipment such as the blood warmer, without affecting the stability of the transmembrane pressure and without causing hemolysis.

It should be appreciated that various changes and modifications can be made without departing from the scope of the appended claims.

What is claimed is:

1. A fluid flow control device comprising
   a housing peripherally enclosing an interior area,
   normally planar flexible wall means extending across said interior area to compartmentalize said interior area into first and second chambers,
   means for forming a first upstanding ridge in said first chamber terminating in a generally planar first surface which faces said flexible wall means in a normally noncontiguous relationship,
   means for forming second and third upstanding ridges in said first chamber positioned, respectively, concentrically inwardly and concentrically outwardly of said first upstanding ridge, forming an inner fluid flow path between said first and second upstanding ridges and an outer fluid flow path between said first and third upstanding ridges, said second and third upstanding ridges terminating, respectively, in generally planar second and third surfaces, each of which faces said flexible wall means in generally said same normally noncontiguous relationship as said first generally planar surface,
   means for forming in said first upstanding ridge an inlet passage having an opening which extends through said first generally planar surface to conduct a first fluid into each of said inner and outer fluid flow paths subject to a determinable pressure,
   means for forming in said first upstanding ridge an outlet passage having an opening which extends through said first generally planar surface in a region spaced from said inlet passage opening to conduct the first fluid from each of said inner and outer fluid flow paths,
   means for forming spaced passages communication with said said second chamber for conducting a second fluid through said second chamber subject to a determinable pressure,
   said flexible wall means being operative in response to fluid pressure differentials between said first and second chambers for displacement out of its normally planar position into farther and closer association with said openings of said inlet passage and said outlet passage in said first upstanding ridge to restrict the conduction of fluid through said inlet and outlet passages to establish and thereafter maintain substantial equilibrum between the pressure of the first fluid and the pressure of the second fluid, and
   said first, second, and third ridges being operative for supporting said flexible wall means in a generally coplanar position while said flexible wall means is displaced in its closest association with said openings of said inlet and outlet passages.

2. A fluid flow control device according to claim 1 and further including means for breaking surface tension between said generally flexible wall means and said generally planar first surface adjacent to said openings of said inlet and outlet passages when said closest association between said flexible wall means and said openings occurs, whereby a continuous conduction of fluid occurs through said openings of said inlet and outlet passages, despite restrictions imposed by said flexible wall means.

3. A fluid flow control device according to claim 1 or 2 where said first, second, and third upstanding ridges are circular.

4. A fluid flow control device according to claim 1 or 2 wherein said opening of said outlet passage in said first ridge is oppositely spaced from said opening of said inlet passage in said first ridge.

5. A fluid flow control device according to claim 4 wherein said first, second, and third upstanding ridges are circular.

* * * * *